(12) United States Patent
Kraemer et al.

(10) Patent No.: US 8,313,921 B2
(45) Date of Patent: Nov. 20, 2012

(54) RECLAIMABLE HYBRID BIOREACTOR

(75) Inventors: Tom Kraemer, Duvall, WA (US);
Charles Kemper, Wilsonville, OR (US);
Jan Allen, Shoreline, WA (US)

(73) Assignee: CH2M Hill, Inc., Englewood, CO (US)

( * ) Notice: Subject to any disclaimer, the term of this patent is extended or adjusted under 35 U.S.C. 154(b) by 1985 days.

(21) Appl. No.: 10/732,162

(22) Filed: Dec. 10, 2003

(65) Prior Publication Data
US 2004/0191755 A1    Sep. 30, 2004

Related U.S. Application Data

(60) Provisional application No. 60/457,500, filed on Mar. 24, 2003.

(51) Int. Cl.
*C12M 1/00* (2006.01)
*C05F 11/08* (2006.01)

(52) U.S. Cl. ............... 435/29; 435/290.1; 435/290.4; 71/9; 71/10; 405/129.5; 405/129.57; 405/129.85; 405/129.95

(58) Field of Classification Search ............... 435/290.1, 435/290.2, 290.3, 290.4, 29; 71/9, 10; 405/129.95, 405/129.5, 129.57, 129.85; C12M 1/00; C05F 11/08; B09B 1/02
See application file for complete search history.

(56) References Cited

U.S. PATENT DOCUMENTS

| | | |
|---|---|---|
| 873,120 A | 12/1907 | Dunstan |
| 988,667 A | 4/1911 | Schodde |
| 1,141,678 A | 6/1915 | Bailey |
| 1,275,222 A | 8/1918 | Chamberlen |
| 1,450,827 A | 4/1923 | Wood |
| 1,734,462 A | 11/1929 | Gottlieb |
| 2,089,801 A | 8/1937 | Kennedy |
| 2,324,545 A | 7/1943 | Svirsky |
| 2,487,228 A | 11/1949 | Feichtmeir |

(Continued)

OTHER PUBLICATIONS

Komilis et al., Waste Management & Research. vol. 17, No. 1pp. 10-19. 1999.*

(Continued)

*Primary Examiner* — David Redding
(74) *Attorney, Agent, or Firm* — Dorsey & Whitney LLP (57) ABSTRACT

A method of biodegrading municipal solid waste includes providing a quantity of municipal solid waste and promoting anaerobic digestion in the quantity of municipal solid waste by methanogenic organisms to produce methane. The methane production is monitored and when it is determined that production of methane from the quantity of municipal solid waste has subsided, aerobic digestion of the quantity of municipal solid waste is promoted. A gas collection system in operative association with the quantity of organic waste collects biogas and the biogas is monitored and the rate of gas collection is adjusted as necessary to maximize methane collection. A leachate collection system collects leachate from the quantity of municipal solid waste and circulates the leachate back to the quantity of organic waste during the anaerobic digestion and aerobic digestion steps. The leachate is preferably supplemented with liquid as necessary to maintain the moisture content of the quantity of municipal solid waste at at least the field capacity of the municipal solid waste. The leachate collection and distribution system may further be used for balancing pH or varying the nitrogen, phosphorous, potassium, calcium, magnesium, chlorine, sulfur, iron, copper, manganese, zinc, molybdenum, nickel or vanadium content of the municipal solid waste during biodegradation. A porous pavement layer may be constructed over the leachate collection system to protect the leachate collection system and bottom lining during operation and excavation of the wastes.

26 Claims, 5 Drawing Sheets

U.S. PATENT DOCUMENTS

| | | | |
|---|---|---|---|
| 2,491,223 A | 12/1949 | Stadlman |
| 2,504,287 A | 4/1950 | Ward |
| 2,507,848 A | 5/1950 | Bashaw |
| 2,514,767 A | 7/1950 | Kennedy |
| 2,547,743 A | 4/1951 | Burr et al. |
| 2,550,401 A | 4/1951 | Boosey |
| 2,607,925 A | 8/1952 | De Puy |
| 2,836,833 A | 6/1958 | Carlson |
| 3,031,826 A | 5/1962 | Brimberg et al. |
| 3,042,210 A | 7/1962 | Hattori |
| 3,212,416 A | 10/1965 | Boersma |
| 3,595,224 A | 7/1971 | Walter |
| 3,653,845 A | 4/1972 | Moravec |
| 3,674,149 A | 7/1972 | Donalson |
| 3,995,331 A | 12/1976 | Fotre et al. |
| 4,257,892 A | 3/1981 | Boersma |
| 4,323,367 A | 4/1982 | Ghosh |
| 4,396,402 A | 8/1983 | Ghosh |
| 4,430,021 A | 2/1984 | Wagner |
| 4,777,674 A | 10/1988 | Payton et al. |
| 4,871,451 A | 10/1989 | Piskula |
| 4,883,590 A | 11/1989 | Papp |
| 4,943,100 A | 7/1990 | Emberson |
| 5,015,371 A | 5/1991 | Webb |
| 5,181,803 A | 1/1993 | Smith et al. |
| 5,265,979 A | 11/1993 | Hansen |
| 5,271,107 A | 12/1993 | Gof et al. |
| 5,285,539 A | 2/1994 | Anderson et al. |
| 5,288,171 A | 2/1994 | Smith et al. |
| D350,598 S | 9/1994 | Wise et al. |
| 5,356,452 A | 10/1994 | Fahey |
| 5,361,430 A | 11/1994 | Wise |
| 5,406,655 A | 4/1995 | Sahlin |
| 5,419,602 A | 5/1995 | VanHoose |
| 5,429,454 A | 7/1995 | Davis et al. |
| 5,491,850 A | 2/1996 | Kiester |
| D370,528 S | 6/1996 | Kiester |
| 5,562,586 A | 10/1996 | Hyde-Smith |
| 5,564,862 A | 10/1996 | Markels, Jr. |
| 5,584,904 A * | 12/1996 | Dalos ................. 71/9 |
| 5,605,417 A | 2/1997 | Englert et al. |
| 5,636,941 A | 6/1997 | Davis et al. |
| 5,758,462 A | 6/1998 | Finn |
| 5,855,664 A | 1/1999 | Bielecki et al. |
| 5,857,807 A | 1/1999 | Longo, Sr. |
| 5,888,022 A | 3/1999 | Green |
| 5,975,801 A | 11/1999 | Burns, Sr. et al. |
| 5,984,580 A | 11/1999 | Ham et al. |
| 6,024,513 A | 2/2000 | Hudgins et al. |
| D422,345 S | 4/2000 | Dixon |
| 6,056,800 A * | 5/2000 | Carter, IV ................. 71/9 |
| 6,099,613 A | 8/2000 | Allen et al. |
| 6,117,671 A * | 9/2000 | Yilmaz ................. 435/262 |
| 6,254,770 B1 | 7/2001 | Remon |
| 6,283,676 B1 | 9/2001 | Hater et al. |
| 6,334,737 B1 * | 1/2002 | Lee ................. 405/129.5 |
| 6,364,572 B1 | 4/2002 | Hudgins et al. |
| 6,386,796 B1 | 5/2002 | Hull |
| 6,398,958 B1 | 6/2002 | Hater et al. |
| 6,471,443 B1 | 10/2002 | Renaud |
| 6,481,929 B1 * | 11/2002 | Layton et al. ............. 405/129.95 |
| 6,555,359 B2 * | 4/2003 | Cummings ................. 435/267 |
| 6,558,081 B2 | 5/2003 | Hull |
| 2001/0044566 A1 | 11/2001 | Bruno et al. |
| 2002/0067953 A1 | 6/2002 | Ankeny et al. |
| 2002/0111527 A1 | 8/2002 | Bruno et al. |

OTHER PUBLICATIONS

Palmisano & Barlaz, Microbiology of Solid Wastes, CRC Press Inc., 1996, pp. 37, 76, 96, 97.

Speece, Toxicity, in D.P. Chynoweth and R. Isaacson (eds.), Anaerobic Digestion of Biomass, Elsevier Science, London, 1987, pp. 109-140.

* cited by examiner

RECLAIMABLE HYBRID BIOREACTOR

RELATED APPLICATIONS

This application claims priority from U.S. Provisional Patent Application Ser. No. 60/457,500, filed Mar. 24, 2003, entitled "Reclaimable Hybrid Bioreactor Landfill."

TECHNICAL FIELD

The present invention is directed toward solid waste landfills, and more particularly to a reclaimable hybrid bioreactor landfill.

BACKGROUND ART

For generations municipal solid waste was disposed of by depositing it in landfills. As an understanding of the potential for air and groundwater pollution from landfills developed, landfill technology evolved to include lining the landfill with a substantially impervious boundary and covering the landfill with a permeable or impermeable daily cover. When the landfill reached its capacity, traditionally the landfill would be covered with a substantially impermeable barrier and vertical vents would be installed to release gasses generated in the biodegradation of the landfilled municipal solid waste. Typically the solid waste would degrade anaerobically and the primary gas produced during this anaerobic decomposition was methane. Any biodegradation taking place in the landfill would proceed slowly, meaning it took many years for the landfill to stabilize such that methane production substantially ceased and the landfill reached its maximum settlement.

In the last few decades landfill operators have taken a more active role in promoting biodegradation of the deposited municipal solid waste material. The term "bioreactor landfill" has come into general use in the past decade to denote a landfill that is operated in such a way as to enhance the decomposition of municipal solid waste rather than simply contain it. Recirculation of leachate collected at the bottom of the landfill has been the primary method of enhancing the rate of waste decomposition. Introduction of additional liquids has also been used to increase the landfill moisture content to an optimal level for biodegradation of the organic materials in the municipal solid waste. In recent years, an operational definition of "bioreactor landfill" has become a landfill that adds (or is designed and equipped to add) water in addition to recirculating leachate. The USEPA essentially adopted this definition for bioreactor landfills in its Landfill MACT Rule governing air emission controls at municipal solid waste landfills. (40 CFR Part 63 National Emission Standards for hazardous Air Pollutants: Municipal Solid Waste Landfills, Fed Reg. Vol. 68, No. 11, p. 2227 (Jan. 16, 2003)). The bioreactor landfill concept encompasses both anaerobic and induced aerobic decomposition processes as well as "hybrid" processes in which aerobic conditions are induced initially in order to minimize the acid production phase of a subsequent anaerobic decomposition phase.

A number of patents are directed to hybrid bioreactor landfills and teach that promoting aerobic biodegradation followed by anaerobic biodegradation under controlled conditions can maximize the speed of biodegradation and therefore result in more efficient volume reduction and stabilization of municipal solid wastes. Representative patents are Hater, U.S. Pat. No. 6,283,676; Ham, U.S. Pat. No. 5,984,580; and Hudgins, U.S. Pat. No. 6,364,572.

The Hater patent contains a useful summary of prior art efforts to increase the efficiency of bioreactor landfills. Hater instructs that the prior art focused extensively on leachate recirculation and maintaining a high moisture content in the municipal solid waste. Hater teaches in addition to maintaining a high moisture content in waste, the desirability of adding materials to accelerate the aerobic or anaerobic decomposition of waste material. Representative additives include sludge, animal manure, fermenter byproducts as well as nutrients such as phosphorous, phosphoric acid, biosolids phosphate buffer and the like which may be added either directly to the waste or added to liquids applied to the waste.

Ham, in addition to teaching the desirability of leachate recirculation to promote efficient biodegradation and collection of methane resulting from anaerobic digestion, teaches that the efficiency of biodegradation can be improved by comminuting solid waste particles to an approximately uniform particle size distribution.

Green, U.S. Pat. No. 5,888,022, while directed exclusively to aerobic digestion, teaches the desirability of controlling temperature within the aerobic digester by controlling the rate of airflow through the digester. Green further teaches the desirability of adding nutrients such as nitrogen, phosphates and carbon sources by injection wells to maintain optimal levels of microbial growth for aerobic digestion. Green teaches that maintaining the aerobic digestion in a temperature range of 130°-150° F. (54° to 65° C.) can substantially eliminate pathogens from a landfill.

While the prior art discussed above is generally concerned with optimizing the biodegradation processes in order to more efficiently stabilize and compact municipal solid wastes, the prior art fails to suggest a method which optimizes methane production and accelerates stabilization and compaction of the landfill while minimizing the risk of fire which has plagued prior art hybrid and aerobic digestion techniques. Furthermore, the prior art fails to teach a municipal solid waste landfill system providing a number of bioreactor cells enabling the efficient biodegradation and methane recovery of mixed municipal solid wastes as well as source separated municipal solid wastes. Finally, the prior art fails to provide bioreactor cells which can be efficiently reclaimed for reuse as needed.

The present invention is directed toward overcoming one or more of the problems discussed above.

SUMMARY OF THE INVENTION

A first aspect of the present invention is a method of biodegrading municipal solid waste. As used herein, "municipal solid waste" means solid waste typically collected as part of a municipal garbage collection system and typically includes in combination household wastes, food wastes, lawn wastes, office generated waste and may further include amounts of industrial generated wastes and scrap material. Municipal solid waste is further intended to include bio-solids and sludges recovered from sewage treatment plants. The term municipal solid waste also includes mixed wastes, such as typical unseparated household waste and source separated wastes such as organics generated by sewage treatment plants and food wastes generated by restaurants and food processing facilities. The method of biodegrading municipal solid waste includes providing a quantity of municipal solid waste and promoting anaerobic digestion of the quantity of municipal solid waste by methanogenic organisms to produce methane. The methane production is monitored and when it is determined that production of methane from the quantity of municipal solid waste has subsided, aerobic digestion of the quantity of municipal solid waste is promoted. The method may further include prior to promoting the anaerobic digestion of the municipal solid waste, determining at least one of the following properties of the municipal solid waste: decomposable organics content, moisture content, bulk density, volumetric pore space, nitrogen content, pH, phosphorous content, potassium content, calcium content, magnesium content, chlorine content, sulfur content, iron content, copper content, manganese content, zinc content, molybdenum content, nickel content and vanadium content. The method may further include amending the quantity of organic waste as necessary to bring the at least one property within select parameters before promoting anaerobic digestion. Alternatively or in addition, at least one of the above listed properties of the municipal solid waste may be monitored during anaerobic digestion and the quantity of municipal solid waste may be amended as necessary during anaerobic digestion to bring the at least one property within select parameters.

In a preferred embodiment, pH of the quantity of municipal solid waste is monitored during the anaerobic digestion step and the pH is adjusted as necessary to maintain the pH high enough to promote the growth of methanogenic organisms. The pH should be maintained above 5, and is preferably maintained in a range between 6.8 and 7.4. The method may further include collecting the methane produced in the anaerobic digestion step using a gas collection system in operative association with the quantity of organic waste and monitoring and adjusting the rate of gas collection as necessary to maximize methane collection. The method preferably further includes providing a leachate collection system for collecting leachate from the quantity of municipal solid waste and circulating the leachate back to the quantity of organic waste during the anaerobic digestion and aerobic digestion steps. The leachate is preferably supplemented with liquid as necessary to maintain the moisture content of the quantity of municipal solid waste at at least the field capacity of the municipal solid waste. The leachate collection and distribution system may further be used for balancing pH or varying the nitrogen, phosphorous, potassium, calcium, magnesium, chlorine, sulfur, iron, copper, manganese, zinc, molybdenum, nickel or vanadium content of the municipal solid waste during biodegradation.

A second aspect of the present invention is a method of biodegrading municipal solid waste that includes providing a bioreactor cell comprising a leachate collection and recirculation system and a gas collection and distribution system. A quantity of municipal solid waste is provided and at least one of the following properties of the quantity of municipal solid waste is determined: decomposable organics content, moisture content, nitrogen content, pH, phosphorous content, potassium content, calcium content, magnesium content, chlorine content, sulfur content, iron content, copper content, manganese content, zinc content, molybdenum content, nickel content and vanadium content. The quantity of municipal solid waste is amended as necessary to bring the at least one property within select parameters. The quantity of municipal solid waste is loaded into the bioreactor cell in operative association with the leachate collection and recirculation system and the gas collection and delivery system. Anaerobic digestion of the quantity of municipal solid waste is then promoted by methanogenic organisms to produce methane. Leachate collected by the leachate collection and recirculation system is recirculated back to the quantity of municipal solid waste. The liquid of the leachate collection and recirculation system is supplemented as necessary to maintain the liquid content of the quantity of municipal solid waste at its field capacity. Methane produced by the anaerobic digestion is collected using the gas collection and delivery system and the amount and concentration of the methane collected is monitored. Upon determining that production of methane from the quantity of municipal solid waste has subsided, aerobic digestion of the quantity of municipal solid waste is promoted by providing air to the quantity of municipal solid waste using the gas collection and delivery system. The method preferably further includes monitoring the temperature of gas collected from the organic waste during aerobic digestion and maintaining the temperature within select parameters by varying the quantity of air provided. Amendment of the quantity of municipal solid waste to bring the at least one property within select parameters may be performed by supplementing the liquid of the leachate collection and recirculating system.

A further aspect of the present invention is also a method for disposal of a solid waste. The method comprises providing a plurality of bioreactor cells, each cell including a leachate collection and recirculation system and a gas collection and delivery system. A quantity of one of a source separated solid waste or a mixed solid waste is provided to one of the bioreactor cells in operative association with the leachate collection and recirculation system and the gas collection and delivery system. Anaerobic digestion of the quantity of waste is promoted by methanogenic organisms to produce methane. Leachate is recycled to the quantity of waste using the leachate collection and recirculation system. The liquid of the leachate collection and recirculation system is supplemented as necessary to maintain the liquid content of the quantity of organic waste at its field capacity. Methane produced during anaerobic digestion is collected using the gas collection and delivery system and the methane collected is monitored to track the quantity of methane produced. Upon determining that production of methane from the quantity of waste has subsided, aerobic digestion of the quantity of waste is promoted by providing air to the quantity of organic waste using the gas collection and delivery system.

Yet another aspect of the present invention is a reclaimable bioreactor landfill cell having a low permeability bottom lining configured to direct leachate deposited on the low permeability bottom lining to at least one collection area. A leachate drainage pipe is operatively associated with each collection area to receive leachate deposited on the low permeability bottom lining. A porous pavement layer overlies the leachate drainage pipe. A porous draining media may be disposed between the low permeability bottom lining and the porous pavement layer, with each leachate drainage pipe being embedded in the porous drainage media. A plurality of perforated distribution pipes preferably provided in fluid communication with each leachate drainage pipe to distribute leachate from the at least one collection area to municipal solid waste resting upon the porous pavement layer. The porous pavement layer may be made of asphalt or cement concrete, with the asphalt including a plurality of drains in communication between the top surface of the asphalt or cement concrete and the porous drainage media. Alternatively, the porous pavement layer may be made of a roller-compacted concrete as part of a pavement system reinforced with high-strength geo-composites. The porous pavement layer is preferably configured to be removable from the porous drainage media to provide access to the bottom lining.

The system preferably further includes providing a landfill in proximity to the plurality of bioreactor cells. Biodegraded mixed solid waste is recovered from the bioreactor cells and deposited in the landfill. The system may further include providing a screening and storage repository for biodegraded source separated solid waste in proximity to the plurality of bioreactor cells and depositing biodegraded source separated solids collected from the bioreactor cells in the storage repository after screening. The leachate collection and recirculation system includes leachate collection pipes underlying the quantity of waste being treated. A permeable pavement layer preferably overlies the leachate collection pipes for supporting the quantity of waste during biodegradation and to allow excavation equipment to operate in the cell to remove the degraded wastes without damaging the underlying leachate collection pipes or bottom lining system.

DETAILED DESCRIPTION OF THE PREFERRED EMBODIMENT

Figure 1:
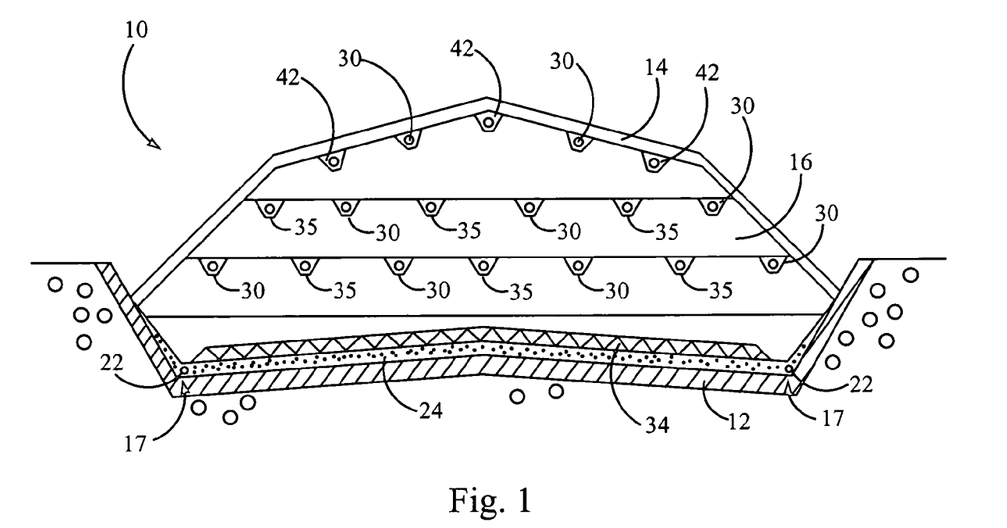
FIG. 1 is a cross-section of a reclaimable bioreactor landfill cell in accordance with the present invention.

A complete and operational reclaimable bioreactor landfill cell 10 is shown in cross-section in FIG. 1. The reclaimable bioreactor landfill cell 10 includes a bottom lining system 12 and a cover 14 containing a quantity of municipal solid waste 16. The bottom lining system 12 should be essentially impervious to liquids. The lining system may simply be a layer of clay or some other seal material. Preferably, the lining system 12 consists of a two layer lining with a witness zone between the linings and sensors to detect leaks in the upper lining. The bottom lining system is configured to direct liquids including leachate received thereon to at least one collection area. As shown in FIG. 1, there are two collection areas 17. The cover 14 should be of low permeability to prevent air intrusion during an anaerobic stage and odor emission during an aerobic stage of biodegradation. The final cover may consist of a low permeability clay used alone or in combination with a removable polymer membrane to ensure isolation of the municipal solid waste within the bioreactor cell.

Figure 2:
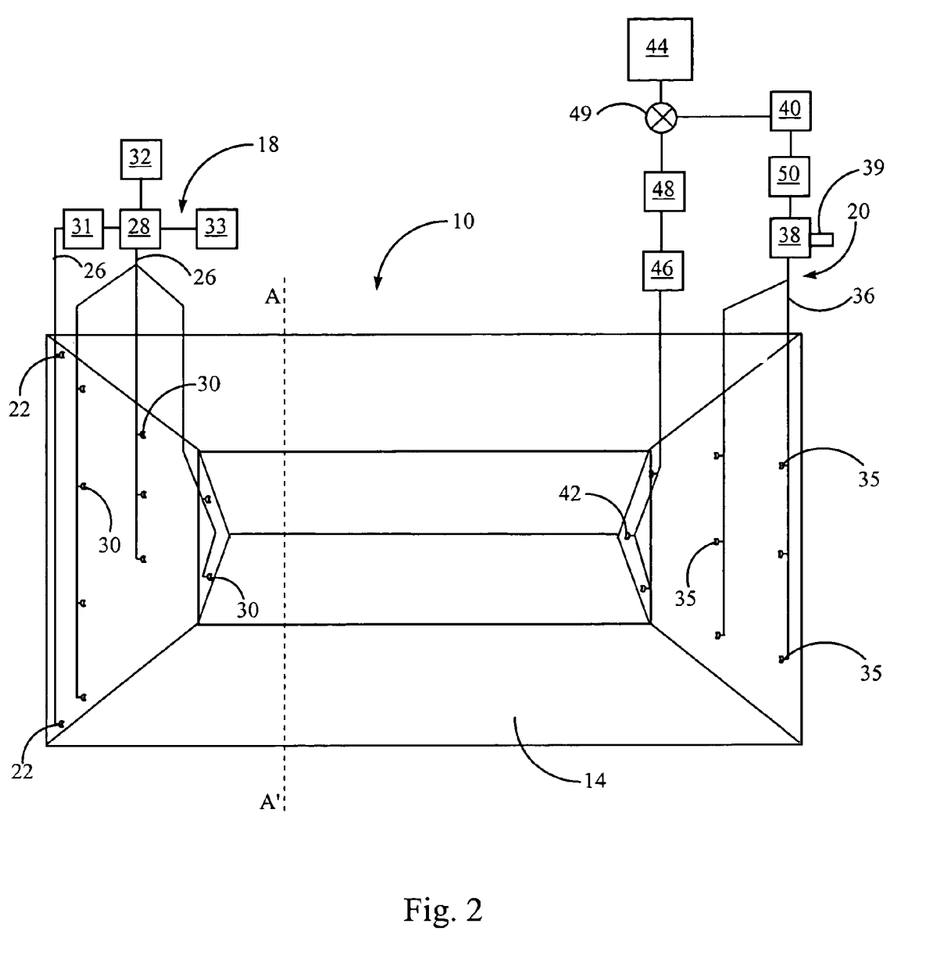
FIG. 2 is a plan view of the reclaimable bioreactor landfill cell of FIG. 1.

The reclaimable bioreactor landfill cell 10 further includes a leachate collection and recirculation system 18 and a gas collection and delivery system 20, which are shown schematically in FIG. 2. Referring to FIG. 1, the leachate collection and recirculation system 18 consists of leachate drainage pipes 22 embedded in a porous drainage media 24, which is typically a layer of gravel or some other porous material. The leachate drainage pipes 22 are preferably perforated and are located at the collection areas 17 within the drainage media 24 to allow for collection of the leachate in the perforated pipes. The leachate drainage pipes 22 are in fluid communication with a conveyance pipe 26, a pump 28 and perforated distribution pipes 30 spaced along essentially horizontal planes between layers of the quantity of municipal solid waste 16. Monitors 31 are in communication with the leachate collection and recirculation system to provide monitoring of properties such as temperature, pH and nutrient content. A liquid supply 32 provides liquid to supplement the leachate, as needed. A buffer/nutrient supply 33 provides buffer and nutrients to the leachate as required. Active temperature controls can also be provided in communication with the leachate collection and recirculation system for colder climates where heating the leachate may increase settlement and gas production. Temperature management is more critical during the aerobic phase than the anaerobic, but is an important consideration for the anaerobic phase as well as the aerobic because temperature greatly affects the rate of biodegradation. In general, the overall process kinetics double for every 10° C. increase in operating temperature. (Palmisano, A. and Barlaz, M., Microbiology of Solid Wastes, CRC Press Inc., 1996, p. 96). If in a cold climate, design of the landfill configuration and waste placement practices to minimize surface area and selection of landfill cover materials and thickness for their thermal properties can and should include considerations for minimizing heat loss.

A porous pavement layer 34 overlies the leachate drainage pipes 22 and drainage media 24. Asphalt or roller-compacted concrete as part of a pavement system reinforced with high-strength geo-composites is a preferred porous pavement layer 34. Covered drains may also be provided through the porous pavement layer to facilitate the flow of leachate to the drainage media 24 and leachate drainage pipes 22. The essential properties of the porous pavement layer 34 are ready conveyance of leachate to the draining media and durability to withstand scraping by and the weight of earth moving equipment as municipal solid waste is added to the reclaimable bioreactor cell and biodegraded municipal solid waste is removed from the reclaimable bioreactor cell. The porous pavement layer 34 is preferably removable and replaceable in the event repairs to the lining system 12 become necessary.

The gas collection and delivery system 20 includes a plurality of perforated collection and delivery pipes 35 disposed in horizontal planes within the quantity of municipal solid waste 16 and alternating with the liquid distribution pipes 30. In this manner withdrawal of leachate through the gas collection and distribution pipes 35 is minimized. The gas collection and distribution pipes 35 are connected to conveyance pipes 36 which in turn are in communication with a reversible exhauster/blower 38 to alternatively withdraw biogas from the reclaimable bioreactor cell 10 or to supply air to the reclaimable bioreactor cell 10 through ambient air inlet 39. The exhauster/blower 38 may be in turn connected to a biogas processing facility 40 for processing of biogas including methane recovered during anaerobic digestion, as will be described in greater detail below. Exhaust pipes 42 are provided adjacent the landfill cover 14 and can be used alternatively for withdrawing biogas during the anaerobic phase and conveying it to the biogas processing facility 40 or for use during aerobic digestion to deliver residual gas to a biofilter 44. An exhauster 46 is in fluid communication with the exhaust pipes 42 to maintain negative pressure therein. Sensors 48 are in communication with the exhaust pipes 42 to monitor temperature, exhaust volume, pressure, methane concentration and carbon dioxide concentration. Other properties may be monitored as well. Valve 49 alternatively directs the exhaust to the biogas processing facility 40 or the biofilter 44. Additional sensors 50 are in communication with the conveyance pipe 36 to monitor methane concentration, $CO_2$ concentration, exhaust volume, pressure, temperature, $O_2$ and volumetric flow.

Figure 3A:
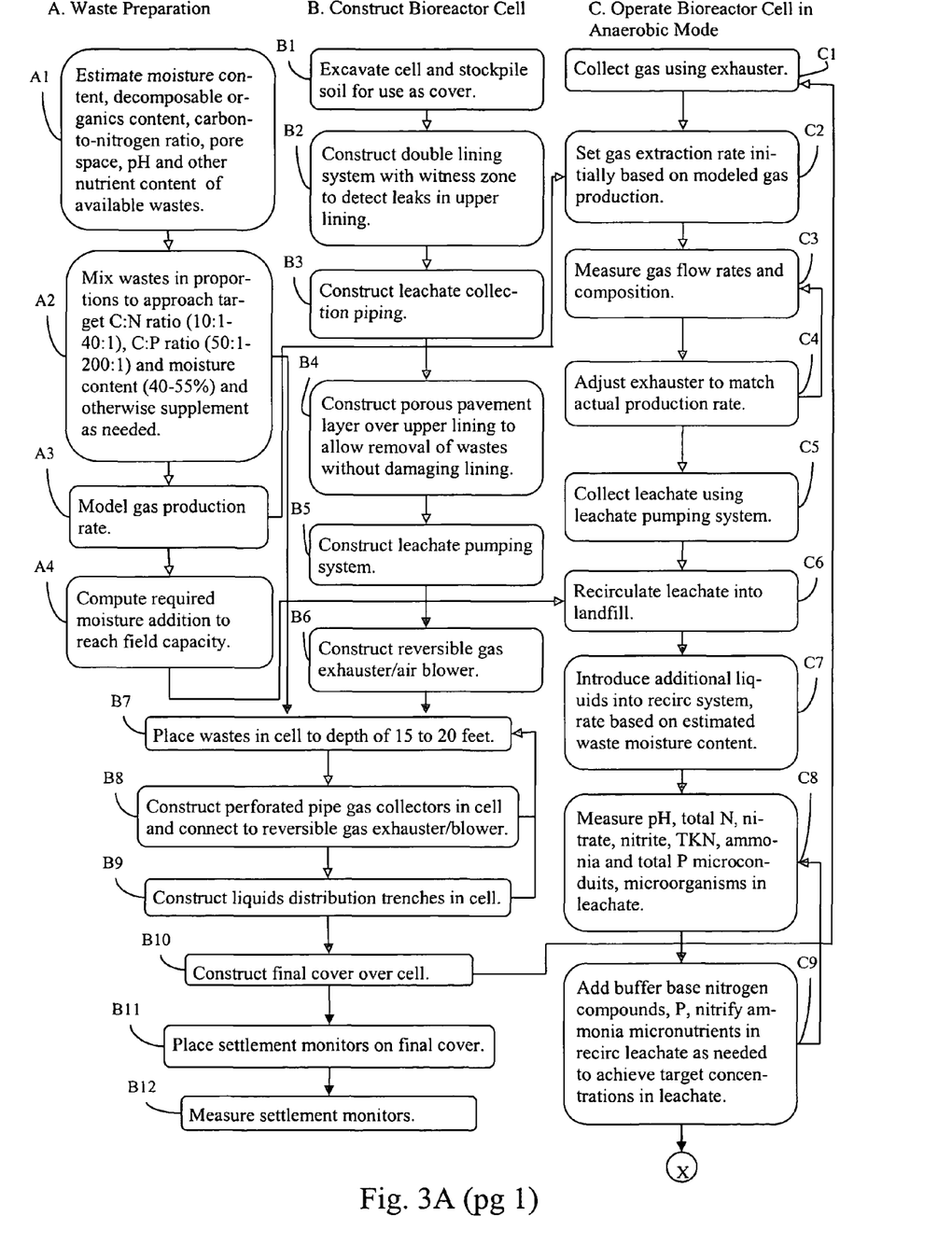
FIGS. 3A and 3B are a flowchart of a method of biodegrading municipal solid waste in accordance with the present invention.
Figure 3B:
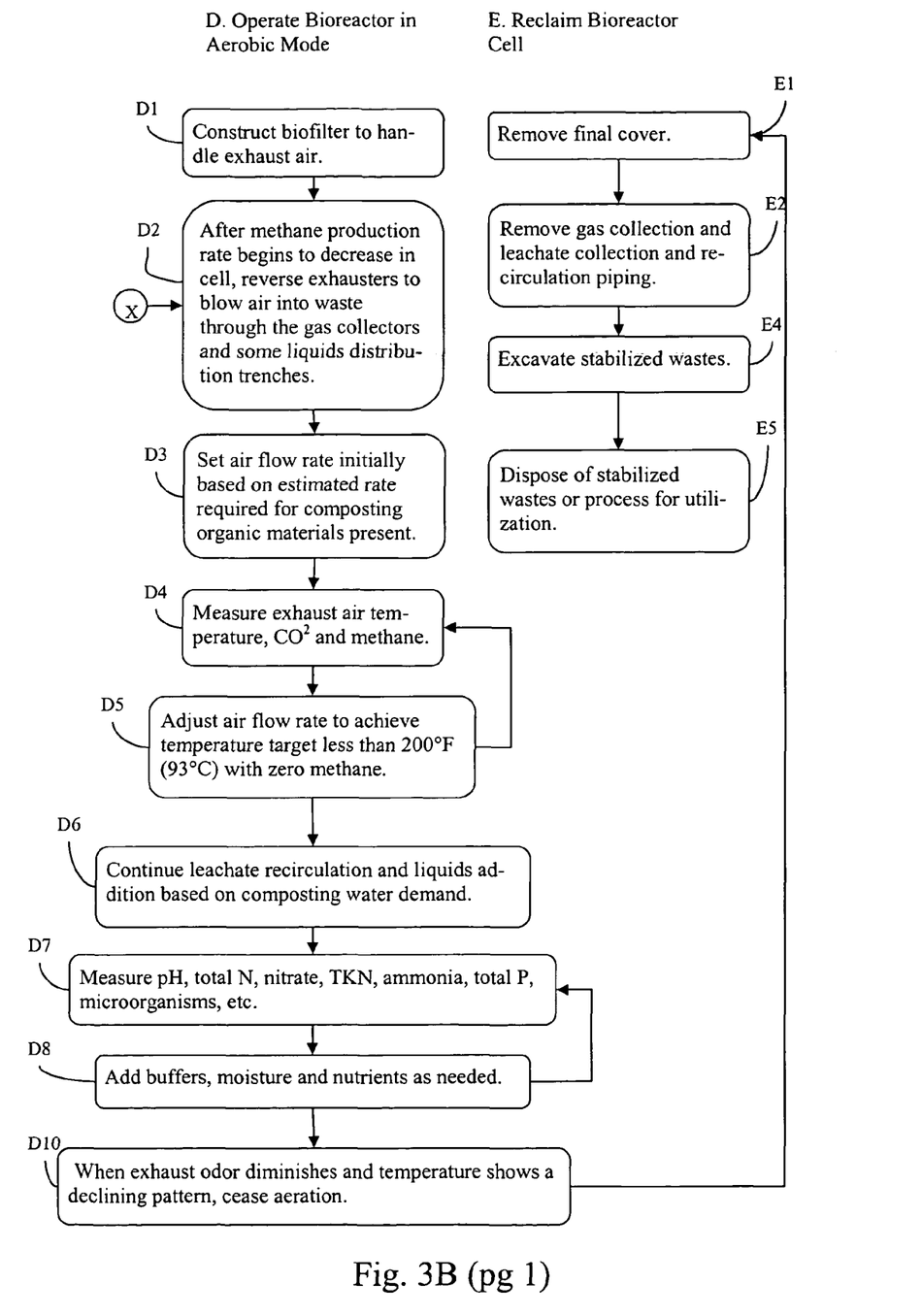

A method of constructing the reclaimable bioreactor landfill cell 10 is described in Column B of the flowchart of FIG. 3. Construction begins at step B1 by excavating a foundation for the cell and storing the excavated soil for use as cover during loading of the cell. Next in step B2 a double lining system 12 including a witness zone for leak detection is installed. In step B3 the leachate drainage pipes 22 are located and the drainage media 24 is laid in place. Next, in step B4 the porous pavement layer 34 is installed. In step B5 the leachate drainage pipes are connected to the conveyance pipe 26 and the pump 28. In step B6 the gas collection and delivery system 20 can also be assembled, although the gas collection/distribution pipes cannot be put in place until a lift of municipal solid waste is installed. In step B7 selected municipal solid waste is placed in the cell at a depth of 10-20 feet. Next, steps B8 and B9 include installing a first horizontal layer of liquid distribution pipes or trenches 30 and gas collection/distribution pipes 35 which are laid in place over the first lift. One or more additional lifts (two as shown in FIG. 2) may be laid upon this first lift with additional rows of leachate distribution pipes 30 and gas collection/distribution pipes 35 placed thereon. After installation of a top lift of municipal solid waste, leachate distribution pipes 30 are put in place and exhaust pipes 42 are put in place as illustrated in FIG. 1 and in step B10 the impermeable landfill cover 14 is installed.

In step B11 settlement monitors are associated with the landfill cover 14 and they are initially measured in step B12. Settlement of solid wastes in demonstration project bioreactors has been irregular. Initial settlement can be quite large within one to two months of filling the cell; this can be followed by a period of secondary settlement over an extended period of time. Reported total settlement during anaerobic decomposition ranges from 15 to 40 percent.

Bioreactor landfill settlement presents several design challenges:
- The final cover must be designed to accommodate rapid settlement of the waste without being physically damaged.
- Gas and leachate collection pipes must be designed to accommodate differential settlement of the waste.
- Compression of wastes at lower levels in the bioreactor can create low permeability layers that impede the flow of leachate and gas through the wastes.

Settlement is important to measure not only because it is indicative of the rate of decomposition in the landfill, but because it is a direct measurement of the creation of value to the landfill owner in the form of airspace.

In order to minimize ponding of storm water, highly permeable material should be used for daily cover during the placing of waste in step B7. If the soil excavated from the cell foundation is sufficiently porous, it may be used as the permeable cover. Other recommended alternative types of cover include mulched or composted yard waste, foam or geotextiles. Reducing the volume of daily cover by using tarps or other alternative covers will also free additional volume for waste storage. Daily cover should be specified to limit overly dense or very finely textured materials. Both of these attributes can cause the cover layers to impede gas and liquid movement.

For optimal performance of the reclaimable bioreactor landfill cell 10, understanding of the composition, physical properties, moisture content and projected quantities of waste materials that will be processed in the reclaimable bioreactor landfill cell are necessary. For example, if waste streams of different materials (e.g. municipal solid waste and biosolids) are to be processed together in the bioreactor, then the relative amounts of each should be known. Among the parameters most important to measure are:
1. Fraction of readily decomposable organic materials (e.g., food waste and paper versus wood waste and inerts), which is analogous to volatile solids measurement or biodegradable fraction, which will allow for projections of settlement and biogas (methane) production.
2. Approximate nitrogen content for managing ammonia and overall nitrogen availability.
3. Initial moisture content, bulk density, and pore space of the waste in place at specified cell operating depth.
4. Rates of delivery both in volume and weight per unit time including seasonal variations which can effect the planning and optimal size for the bioreactor cells.

Prior to step B7, waste preparation should be conducted which is summarized in Column A of the flowchart of FIG. 3. Waste preparation includes at step A1 determining at least one and preferably all of the following properties of the quantity of municipal solid waste being added to the reclaimable bioreactor landfill cell: decomposable organic content, moisture content, pore space, nitrogen content, pH, phosphorous content, potassium content, calcium content, magnesium content, chlorine content, sulfur content, iron content, copper content, manganese content, zinc content, molybdenum content, nickel content and vanadium content. In step A2, the quantity of municipal solid waste is amended as necessary to bring these properties within select parameters. In step A3, based upon the known content of the municipal solid waste, gas extraction rates are initially projected. In addition, in step A4 moisture addition necessary to reach field capacity is calculated.

Measurement of nutrients should be conducted and, if necessary, deficient nutrients should be added in steps A1 and A2. An overall C:N ratio of between 10:1-40:1 is considered optimal for anaerobic digestion. In addition, adequate supplies of nitrogen and phosphorous are necessary for anaerobic digestion. Total nitrogen and phosphorous requirements are estimated to be a range of about 0.6-1.8% and 0.012-0.036%, respectively, of the biodegradable volatile solids in the waste. A carbon to phosphorous ratio of between 50:1-200:1 is desirable. Optimum and maximum (i.e., toxic) ammonia concentrations are 700 mg/l and 3000 mg/l, respectively. Other nutrients reported to be required for efficient biodegradation of municipal wastes include sodium, potassium, calcium, magnesium, chlorine and sulfur. (Palmisano, A. and Barlaz, M., Microbiology of Solid Wastes, CRC Press Inc., 1996, p. 97, the contents of which are incorporated in their entirety herein.)

Most of these nutrients are typically present in mixed municipal solid wastes in adequate concentrations, but for some organic waste streams it may be necessary to analyze for them and supplement the waste stream. In addition, several micro-nutrients have been identified as necessary in anaerobic digestion, including iron, copper, manganese, zinc, molybdenum, nickel and vanadium. (Speece, R. F., Toxicity, in D. P. Chynoweth and R. Isaacson (eds.), Anaerobic Digestion of Biomass, Elsevier Science, London, 1987, pp. 4-29109-140.) The quantity of these micro-nutrients should also be determined and supplemented as needed to fit predetermined parameters.

With respect to pore space, it is essential that gas and liquid be able to circulate within each lift of the municipal solid waste. While the precise porosity required to achieve this result through the anaerobic and aerobic phases will be a function of the municipal solid waste source(s), an initial volumetric pore space of about 10% or greater is believed adequate to provide the necessary air and leachate circulation. Preferably an adequate and sufficiently uniform porosity to provide circulation throughout the municipal solid waste can be achieved by mixing waste materials from different sources as required.

pH management may also be required because of the potential for acids to accumulate in the early phases of anaerobic decomposition. Biodegradation in a landfill is primarily through anaerobic digestion of complex carbohydrates. It has been estimated that cellulose and hemicellulos make up over 90% of the biochemical methane potential of municipal solid waste. (Palmisano, A. and Barlaz, M., Microbiology of Solid Wastes, CRC Press Inc., 1996, p. 76.) This material is configured to be degraded in a two or three step process consisting of hydrolysis of the sugar polymers to monomers, followed by organic acid production (primarily acetate) followed by production of methane and carbon dioxide. In the early stages of decomposition, it is possible for the acid producing organisms, which are different from the methanogens, to dominate the system, produce excess acid and prevent the methanogens from thriving. This is because methanogens are most active in a pH range of 6.8 to 7.4 and are inactivated or killed below a pH of about 5. (See Palmisano and Barlaz, supra.) As a result, attention to pH and buffering requirements is most important during the early stages of leachate recirculation when rapid growth of acid-forming organisms can lead to an accumulation of acids, low pH and the inhibition of methanogenic organisms. Ideally, leachate pH is controlled by making sure the waste materials have sufficient buffer salts to prevent the pH from falling below 6 and thereby inhibiting methanogenesis during placement of the materials in the reclaimable bioreactor landfill cell. Thus, if necessary based on the assessment of the composition of incoming waste, buffering materials (which may be suitable waste materials) could be added as the wastes are placed in the landfill. Leachate pH adjustment may also be accomplished in response to low pH measurements in the re-circulated leachate by adding lime or sodium hydroxide 33 to the leachate during recirculation. As a result, the leachate recirculation system should be designed both to monitor pH and include a supply of lime or sodium hydroxide in communication with the leachate recirculation system if pH buffering becomes necessary. Frequent monitoring of the pH is necessary though the frequency may not need to be more than weekly. Likewise, nutrients in the recovered leachate should be monitored at similar intervals. As with pH management, nutrient management is ideally done by making sure the waste materials added to the landfill have the appropriate concentrations of nutrients and other properties. However, if necessary, nutrients can be added to the quantity of municipal solid waste under treatment by the leachate recirculation system.

Once the reclaimable bioreactor landfill cell is loaded and constructed as described above, biodegradation of the municipal solid waste is begun. The object of the construction of the reclaimable bioreactor landfill cell is to achieve airspace reduction, enhanced biogas (methane) production and in situ leachate treatment while moving the wastes as quickly as possible through a process that results in inert materials (that pose less environmental risk and management effort than municipal solid waste) and useful products, and to reclaim the rapid decomposition area for additional wastes or other purposes. To achieve these results a cell is designed and the method is intended to promote immediate anaerobic decomposition of the municipal solid waste by methanogenic organisms enhanced with moisture recirculation and potentially nutrient addition and pH adjustment. Production of the methane is monitored and when methane production begins to subside, the treatment switches rapidly to aerobic decomposition of the remaining organic materials. By the time aerobic digestion begins, the anaerobic bacteria should have consumed the majority of organic materials in the waste, which reduces the potential for landfill fires in the subsequent aerobic phase. Critical to maximizing anaerobic digestion by methanogenic organisms is preventing the pH level from dropping to a level suppressing the growth of the methanogenic bacteria. Operation of the reclaimable bioreactor landfill cell is best understood with reference to Columns C and D of the flowchart of FIG. 3.

In step C1, operation begins by initiating collection of biogas produced within the reclaimable bioreactor landfill cell. The gas extraction rate is initially based in step C2 upon modeled gas production determined during waste preparation. Actual composition of the extracted gas is measured in step C3 and the rate of gas exhaustion is matched to actual methane production in step C4. Leachate generated during biodegradation is collected using the leachate collection and recirculation system in step C5 and distributed to the solid waste in step C6. In step C7 liquids are added to the recirculation system as needed based on the estimated field capacity of the quantity of municipal solid waste under treatment. If sufficient liquids are present in the municipal solid waste, no additional liquid is required. The content of nutrients and the pH of the leachate are monitored in step C8 and the pH is buffered and nutrients are added as necessary to maintain the properties within select parameters in step C9.

Maintaining adequate moisture content is believed to be the most important operational property determining the effective performance of a bioreactor landfill. Water within the bioreactor landfill transports nutrients, enzymes and microorganisms; dilutes inhibitory compounds; exposes waste surfaces to microbial attack; serves as a reactant in the hydrolysis reactions; and transports pH buffers. Excess water will also displace oxygen in the void spaces within the waste, which promotes development of anaerobic conditions.

Moisture content within a bioreactor landfill is generally discussed using the concept of field capacity, a term landfill engineers borrow from soil scientists. Field capacity is generally defined as the maximum amount of water a sample of waste will retain against gravity through capillary forces. It can be measured in a laboratory by subjecting a saturated waste sample to a suction head of 100 cm water, and then determining the resultant moisture content of the waste. In practice, field capacity is generally understood to be the amount of water that a saturated sample of waste will retain after it has freely drained. Adding water to waste in excess of the field capacity (which will inevitably occur in localized areas due to short circuiting) will result in continuous drainage from the waste.

Estimating the field capacity of the waste in the reclaimable bioreactor landfill cell is important because it allows the bioreactor landfill operator to determine the quantity of water that needs to be added to the cell. The moisture content of the waste should be maintained at or near field capacity; this will result in continuous leachate drainage from the cell and increase the liquid-filled pores within the waste. Field capacity is a function of waste composition, age and density. Typical field capacity values reported in the literature ran from 20 to 53% on a wet weight basis. See Palmisano, A. and Barlaz, M., *Microbiology of Solid Wastes*, CRC Press Inc., 1996, p. 37.

In operating (and planning) the reclaimable bioreactor landfill cell 10 all inputs and outputs of water will need to be monitored and controlled to achieve the optimum moisture content in the waste. These inputs and outputs include:

| | |
|---|---|
| Inputs: | Storm water infiltration (including snowmelt), leachate recirculation, water addition, and initial moisture in the different waste streams. |
| Outputs: | Leachate collection, water vapor in gas collection system, evapo-transpiration from the landfill cover. |

Storm water is controlled by proper landfill surface contouring and final cover, as well as proven run-on and run-off controls that have been developed for normal landfill operation. Leachate recirculation and water addition (if needed) rates are computed based on the water balance for the landfill, computed at least monthly by subtracting the above outputs from inputs.

In addition to water management, optimizing production of methane is integral to the efficient operation of the reclaimable bioreactor landfill cell. Landfill studies suggest that typical anaerobic waste stabilization proceeds in five sequential phases. The quality and quantity of the biogas produced by a bioreactor landfill will vary with each phase and are indicative of the processes occurring in the landfill. The five phases and the characteristics of the gas production in each phase are listed in the following table, along with the typical lengths of time of each phase in a non-bioreactor landfill.

TABLE 1

Phases of Waste Decomposition and Gas Production in Non-bioreactor

| Phase | Description | LFG Production | Length of Time |
|---|---|---|---|
| 1 | Initial - aerobic conditions. | Only $CO_2$ by anaerobic bacteria | Up to 1 week |
| 2 | Transition - $O_2$ is gradually used up and facultative organisms begin to thrive. | Minimal methane production - only in anoxic pockets | 1 to 6 months |
| 3 | Acid forming - landfill ecology is dominated by acid-forming anaerobic and facultative bacteria. pH drops. | Methane production increases as additional anoxic pockets spawn methanogenic colonies | 3 months to 3 years |
| 4 | Methane formation - methanogenic bacteria predominate after entire landfill becomes anoxic and much organic matter decomposed to sugars and acids. | Maximum methane production | 8 or more years |
| 5 | Maturation - Available organic substrate becomes limiting and biological activity declines. | Biogas production goes into a long declining phase, asymptotically approaches zero. | through post-closure period of landfill |

The reclaimable bioreactor landfill cell 10 is intended to achieve the lower end of the time ranges cited in Table 1 for the initial stages (stages 1-3) of decomposition so that the methane formation stage can be achieved within one year or less after placement of waste, with the peak methane production occurring within two years. Within three years it is intended that the methane production should begin to decline and the majority of the organic decomposable waste be consumed. At this point the invention contemplates that the biodegradation switch from anaerobic to aerobic.

Gas flow rate and composition are preferably measured daily, particularly in cases where the methane is intended as an energy source. Methane extraction flow rates from different parts of the landfill will need to be adjusted to extract the amount of methane actually being produced; over extraction is signaled by high $CO_2$ to methane ratios indicating localized aerobic digestion being caused by air intrusion.

As discussed above, as the production of methane subsides, the method of the present invention contemplates switching from anaerobic to aerobic digestion. This phase of operation is illustrated in Column D of the flowchart of FIG. 3. As a first step D1, a biofilter 44 is constructed to handle air exhausted from the reclaimable bioreactor cell 10. At step D2, air is pumped into the bioreactor cell through the gas collection/distribution pipes 35 which stops anaerobic digestion and promotes aerobic digestion. Excess air is captured in exhaust pipes 42 and conveyed to the biofilter 44. The stimulated aerobic digestion will consume the remaining decomposable organic material and render it inert or composted organic matter. It is contemplated that this process will be completed within about 45-85 days. The risk of landfill fire normally associated with aerobic digestion will be minimized since the majority of the easily decomposable materials will have already been anaerobically decomposed. The risk may be further limited by minimizing the depth of the aerated layer and controlling porosity uniformity since ignition points are normally dense, moist and non-porous so heat accumulates without migration.

In order to accommodate both the aerobic and anaerobic digestion, the gas piping 34, 42 must be designed to handle both the maximum biogas production during the anaerobic phase and the required delivery of air during the aerobic phase. The biogas production rate estimate must take into account the acceleration of gas production expected due to efficient bioreactor operation. Studies have indicated that bioreactor operation has increased biogas production 2.1 to 4.5 over conventional landfill operation. For estimation purposes the inventors recommend a methane generation rate of 0.25 $ft^3$/per pound/year can be assumed, which is about 2.5 times a typical rate of 0.1 $ft^3$/pound/year from a wet refuse.

Returning to Column D of the flowchart of FIG. 3, at step D3 the initial rate of supplying air to the reclaimable bioreactor landfill cell during the aerobic phase is initially based on an estimated rate required for composting the organic materials present. At step D4, the air exhausted through the exhaust pipes 42 is monitored to measure temperature, $CO_2$ content and methane production. In step D5 the air flow rate should be maintained to achieve a target temperature for the aerobic digestion and to minimize methane production (which is indicative of anaerobic digestion). Preferably, the temperature is maintained below 200° F. (93° C.) to help minimize the possibility of fire in the landfill.

During aerobic digestion, leachate recirculation and liquid addition, as needed, continues in step D6 based on the composting water demand. In addition, the properties of the leachate are monitored to ensure pH, total nitrogen, nitrate, TKN, ammonia, total phosphorous, micro-nutrients and microorganisms remain within select parameters in step D7. As in the anaerobic phase, the recirculated leachate can be used as a vehicle for adding buffers or nutrients as necessary to maintain the properties within the select parameters in step D8. In step D9, when exhaust odors diminish and temperature monitoring shows a declining pattern aeration can end and the reclaimable bioreactor landfill cell can be reclaimed as described in Column E of the flowchart of FIG. 3. As understood by those skilled in the art, diminishing odor is indicative of volatile fatty/organic acid concentration diminishing, which typifies an end of aerobic digestion. Odor may be characterized by intensity and hedonic tone (e.g., putrescible/silage/fecal/landfill odors, etc.).

The first step E1 in reclaiming of the bioreactor cell is removal of the final cover 14 followed by removal of the exhaust pipes 42, the gas collection and distribution pipes 35 and the leachate distribution pipes 30 at step E2. Thereafter the stabilized municipal solid waste can be excavated at step E3 and either disposed of or processed for utilization in step E4, depending upon the nature of the municipal solid waste being treated.

Table 2 below summarizes the operational parameters and control methods discussed above with respect to anaerobic and aerobic operation of the reclaimable bioreactor landfill cell.

TABLE 2

Operational Parameters and Control Methods

| Parameter | Optimal Condition | Measurement | Control Method |
| --- | --- | --- | --- |
| Waste Composition (putrescible organic content, nitrogen, moisture) | Wastes approaching field capacity with C:N ratio in a target range of 10:1 to 40:1 and C:P in a target range is 50:1 to 200:1 | Composition studies | Mix wastes with varying characteristics to achieve optimal conditions |
| In situ moisture content | Field capacity, assumed to be in a target range of 40-55% | Estimation by water balance with measured inputs/outputs; Piezometers in landfill | Regulation of leachate recirculation and water addition |
| pH | pH = 6.8 to 7.4 | Leachate pH | Buffers in waste or added to recirculated leachate, bases added to recirculated leachate as last resort |
| Nitrogen | Total N >1.2% of COD in leachate, ammonia 700 mg/l and <3,000 mg/l | Leachate nitrate, nitrate TKN and ammonia | Addition of nitrates, nitrification and re-introduction of leachate with high ammonia |
| Phosphorous | >0.024% of leachate COD | Leachate P | Addition of phosphates to recirculated leachate |
| Gas flow, methane, $CO_2$ and oxygen | Maximum gas production, estimated at 0.25 ft$^3$/lb/yr of MSW in place | Real time flow and gas composition with portable instruments at each gas header | Exhauster and valve adjustments to control flow rate to avoid over extraction |
| Air flow (during aerobic stage) | Control temperature to achieve compost temperature below 200° F. (93° C.) (target range is 0.25 cfm/cy to 2.5 cfm/cy) | Temperature probes in composting waste | Blower and valve adjustments - increase flow above stoichiometric minimum to lower temperature |
| Temperature (during anaerobic stage) | Maximum temperature (while maintaining anaerobic conditions) | Leachate and gas temperature | Waste placement to minimize heat loss |
| Settlement | Maximum | Settlement monitors on landfill surface | N/A |

Figure 4:
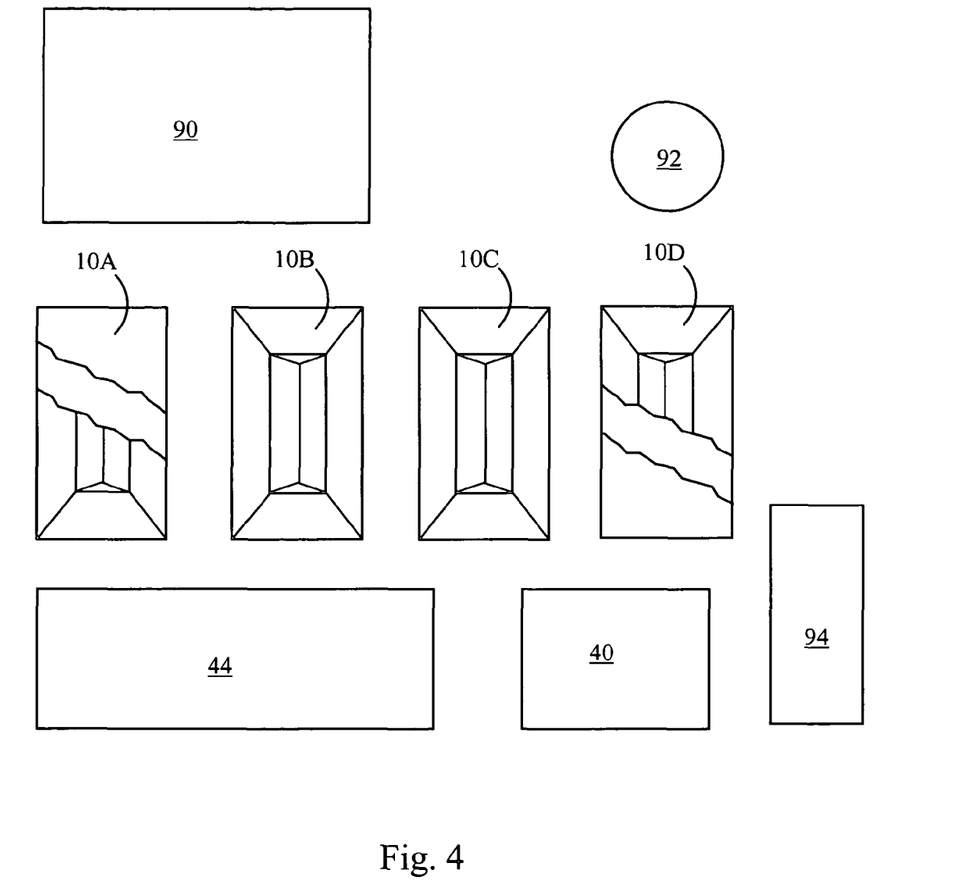
FIG. 4 is a plan view of a municipal solid waste treatment system in accordance with the present invention.

FIG. 4 illustrates a solid waste management system and facility in accordance with the present invention. The facility of FIG. 4 includes a number of bioreactor cells 10A-10D in various phases of operation. More particularly, the cell 10A is in the process of being filled with municipal solid waste. Cell 10B is being operated in an anaerobic mode. Cell 10C is being operated in an aerobic mode. Cell 10D is in the process of being excavated and reclaimed. The facility contemplates the cells being in proximity to a conventional landfill 90. The facility also includes a leachate storage tank 92 which can receive leachate from the leachate collection and recirculation systems of the various cells 10A-10D. This tank can help balance the production and consumption of leachate between the various cells. The facility further includes a repository 94 for receiving treated source separated municipal solid waste. A biofilter 44 is provided for treating air discharged from the cells operating in an aerobic mode. Finally, a biogas processing facility 40 is included.

In addition to the four cells illustrated in FIG. 4, more cells may be provided so that a variety of municipal solid wastes can be biodegraded separately for either recovery or disposal of the biodegraded waste. More particularly, some of the cells may treat mixed municipal solid waste containing a variety of solid waste in addition to organics (e.g., plastics, glass, metal) while others are used for treating source separated municipal solid waste.

Using municipal solid waste as a feedstock for the bioreactor with no separation of food waste or other organics relies upon the reclaimable bioreactor landfill cell 10 to act as a pretreatment system for waste before final disposal in the landfill 90. Because the typical municipal solid waste even after recycling diversions still contains roughly half its original weight in paper, cellulose, vegetation and food, the potential to decompose this material in the reclaimable bioreactor prior to disposal can significantly reduce the volume and mass of waste requiring disposal. In this case, the decomposed inert materials removed from the reclaimable bioreactor landfill cells 10A-10D provide a significantly reduced volume of waste for ultimate disposal in the landfill 90.

Additional reclaimable bioreactor landfill cells can be provided for source separated municipal solid waste. The source separated municipal solid waste includes food waste and other organic material mixed with green waste and other materials to achieve the required physical and chemical properties for efficient anaerobic and aerobic digestion. The feed stocks are collected in a way that limits chemical residues, plastics, glass and metal contaminates. This ensures that the final product meets public health and fertility standards for soil and soil amendment. Bioreactor cells used for source-separated waste are within close proximity to the repository 94 where the treated waste can be screened and stored for later reuse as a salable product. Alternatively the output can be returned to a landfill 90 for ultimate disposal if no viable use or market for the decomposed source separated waste is available.

Because the reclaimable bioreactor landfill cells 10 can be reclaimed and deployed for processing of source separated or mixed municipal solid waste, a site illustrated in FIG. 4 can be operated flexibly, shifting reclaimable bioreactor landfill cells 10A-10D into and out of various types of operation to meet the requirements for treating municipal solid waste and the demands for treated compost material.

The reclaimable bioreactor landfill cell, municipal solid waste management system and the methods for treatment of municipal solid waste disclosed herein are designed not only to achieve air space reduction, enhanced biogas production and in situ leachate treatment, but to move waste as quickly as possible through a process that results in biodegraded materials (that pose less environmental risk and management effort than untreated municipal solid waste) and useable products and reclaim the rapid decomposition area for additional waste or other purposes.

What is claimed is:

1. A method of biodegrading municipal solid waste comprising:
    a. providing a quantity of municipal solid waste to a bioreactor cell;
    b. promoting anaerobic digestion in the quantity of municipal solid waste in the bioreactor cell by methanogenic organisms to produce methane;
    c. determining when the production of methane from the quantity of municipal solid waste subsides; and
    d. following step c, promoting aerobic digestion of the quantity of municipal solid waste in the bioreactor cell.

2. The method of claim 1 further comprising prior to step b:
    a1. determining at least one of the following properties of the municipal solid waste: decomposable municipal solid content, moisture content, nitrogen content, pH, phosphorous content, potassium content, calcium content, magnesium content, chlorine content, sulfur content, iron content, copper content, manganese content, zinc content, molybdenum content, nickel content and vanadium content.

3. The method of claim 2 further comprising following step a1. and prior to step b., amending the quantity of municipal solid waste as necessary to bring the at least one property within select parameters.

4. The method of claim 1 further comprising monitoring at least one of the following properties of the municipal solid waste during step b.: decomposable municipal solid waste content, moisture content, nitrogen content, pH, phosphorous content, potassium content, calcium content, magnesium content, chlorine content, sulfur content, iron content, copper content, manganese content, zinc content, molybdenum content, nickel content and vanadium content.

5. The method of claim 4 further comprising amending the quantity of municipal solid waste as necessary to bring the at least one property within select parameters.

6. The method of claim 1 further comprising during step b., monitoring the pH and adjusting the pH as necessary to maintain the pH high enough to promote growth of methanogenic organisms.

7. The method of claim 6 wherein the pH is maintained between 6.8 and 7.4.

8. The method of claim 1 further comprising:
    b1. collecting the methane produced in step b.

9. The method of claim 8 wherein step b1 is performed by providing a gas collection and delivery system in operative association with the quantity of municipal solid waste and the bioreactor cell, the method further comprising:
    b2. monitoring the content of the gas collected in the gas collection and delivery system and adjusting the rate of gas collection as necessary to maximize methane collection.

10. The method of claim 1 further comprising providing a leachate collection and recirculation system in operative association with the bioreactor cell for collecting leachate from the quantity of municipal solid waste and circulating the leachate back to the quantity of municipal solid waste during steps b and d.

11. The method of claim 10 further comprising supplementing the leachate with liquid as necessary to maintain the moisture content of the quantity of municipal solid waste at at least a field capacity of the quantity of municipal solid waste.

12. The method of claim 5 further comprising a leachate collection and recirculation system operatively associated with the bioreactor cell for collecting leachate from the quantity of municipal solid waste and recirculating the leachate back to the quantity of municipal solid waste during steps b and d, the quantity of municipal solid waste being amended by adding the amendment to the leachate recirculated back to the quantity of municipal solid waste.

13. A method of biodegrading municipal solid waste comprising:
    a. providing a bioreactor cell comprising a leachate collection and recirculation system and a gas collection and delivery system;
    b. providing a quantity of municipal solid waste;
    c. determining at least one of the following properties of the quantity of municipal solid waste: decomposable municipal solid content, moisture content, nitrogen content, pH, phosphorous content, potassium content, calcium content, magnesium content, chlorine content, sulfur content, iron content, copper content, manganese content, zinc content, molybdenum content, nickel content and vanadium content;
    d. amending the quantity of municipal solid waste as necessary to bring the at least one property within select parameters;
    e. loading the quantity of municipal solid waste into the bioreactor cell in operative association with the leachate collection and recirculation system and the gas collection and delivery system;
    f. promoting anaerobic digestion in the quantity of municipal solid waste in the bioreactor cell by methanogenic organisms to produce methane;
    g. recirculating leachate collected by leachate collection and recirculation system to the quantity of municipal solid waste;

h. supplementing the liquid of the leachate collection and recirculation system as necessary to maintain the liquid content of the quantity of municipal solid waste at its field capacity;
i. collecting the methane produced using the gas collection and delivery system;
j. monitoring the collected methane; and
k. upon determining that the production of methane from the quantity of municipal solid waste has subsided, promoting aerobic digestion of the quantity of municipal solid waste in the bioreactor cell by providing air to the quantity of municipal solid waste using the gas collection and delivery system.

14. The method of claim 13 further comprising in step k, monitoring the temperature of gas exhausted from the quantity of municipal solid waste and maintaining the temperature within select parameters by varying the quantity of air provided.

15. The method of claim 13 wherein step d, is performed by supplementing the liquid of the leachate collection and recirculation system.

16. A method for disposal of solid waste comprising:
a. providing a plurality of bioreactor cells, each cell comprising a leachate collection and recirculation system and a gas collection and delivery system;
b. providing a quantity of one of a source separated solid waste and a mixed solid waste to one of the bioreactor cells in operative association with the leachate collection and recirculation system and the gas collection and delivery system;
c. promoting anaerobic digestion in the quantity of one of a source separated solid waste and a mixed solid waste in the one bioreactor cell by methanogenic organisms to produce methane;
d. recycling leachate to the quantity of the one of a source separated solid waste and a mixed solid waste using the leachate collection and recirculation system in the one bioreactor cell;
e. supplementing the liquid of the leachate collection and recirculation system as necessary to maintain the liquid content of the quantity of one of a source separated solid waste and a mixed solid waste at its field capacity in the one bioreactor cell;
f. collecting the methane produced using the gas collection and delivery system;
g. monitoring the collected methane; and
h. upon determining that the production of methane from the quantity of one of a source separated solid waste and a mixed solid waste has subsided, promoting aerobic digestion of the quantity of one of a source separated solid waste and a mixed solid waste by providing air to the quantity of organic waste using the gas collection and delivery system in the one bioreactor cell.

17. The method for disposal of solid waste of claim 16 further comprising providing a landfill in proximity to the plurality of bioreactor cells and depositing biodegraded mixed solid waste in the landfill.

18. The method for disposal of solid waste of claim 16 further comprising providing a repository for biodegraded source separated solid waste in proximity to the plurality of bioreactor cells and depositing biodegraded source separated solids waste in the repository.

19. The method for disposal of solid waste of claim 16 further comprising maintaining each of the plurality of cells in one of a loading, anaerobic, aerobic, reclaim or empty mode.

20. The method for disposal of solid waste of claim 16, wherein the leachate collection and recirculation system comprises leachate collection pipes underlying the quantity of one of a source separated solid waste and a mixed solid waste, the system for disposal of solid waste further comprising a permeable pavement layer overlying the leachate collection pipes for supporting the quantity of waste during biodegradation.

21. The method of claim 1 further comprising the bioreactor cell being located in a ground excavation.

22. The method of claim 21 further comprising forming the bioreactor cell by covering the quantity of municipal solid waste with excavated soil.

23. The method of claim 13 further comprising in step a., providing the bioreactor cell in a ground excavation.

24. The method of claim 23 further comprising following step e, and before step f., covering the quantity of municipal solid waste with excavated soil.

25. The method of claim 16 further comprising each bioreactor cell being located in a ground excavation.

26. The method of claim 25 further comprising forming the bioreactor cell by covering the quantity of one of a source separated solid waste and a mixed solid waste with excavated soil.

* * * * *